United States Patent
Tsuchiya

(10) Patent No.: US 7,683,328 B2
(45) Date of Patent: Mar. 23, 2010

(54) PHOTOGRAPHING CONTROL APPARATUS AND METHOD

(75) Inventor: Keiji Tsuchiya, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 115 days.

(21) Appl. No.: 12/143,490

(22) Filed: Jun. 20, 2008

(65) Prior Publication Data
US 2009/0016492 A1    Jan. 15, 2009

(30) Foreign Application Priority Data
Jul. 9, 2007   (JP) ............................. 2007-179893

(51) Int. Cl.
*G01J 1/42* (2006.01)
(52) U.S. Cl. .................... 250/354.1; 378/116
(58) Field of Classification Search ............. 250/354.1, 250/370.09; 378/115, 116
See application file for complete search history.

(56) References Cited

U.S. PATENT DOCUMENTS

| | | | |
|---|---|---|---|
| 4,774,720 A * | 9/1988 | Carbon ....................... | 378/116 |
| 7,227,926 B2 | 6/2007 | Kameshima et al. ....... | 378/98.9 |
| 7,343,000 B2 | 3/2008 | Kameshima et al. ....... | 378/98.9 |
| 2005/0243967 A1 * | 11/2005 | Inoue ......................... | 378/97 |

FOREIGN PATENT DOCUMENTS

JP    2005-287773    10/2005

* cited by examiner

*Primary Examiner*—David P Porta
*Assistant Examiner*—Marcus H Taningco
(74) *Attorney, Agent, or Firm*—Fitzpatrick, Cella, Harper & Scinto

(57) ABSTRACT

A photographing control apparatus that controls a sensor for accumulating and reading out electric charge in order to obtain an image, includes: a deciding unit adapted to decide a frame period showing an image photographing interval, based on an input of an input unit; a determining unit adapted to determine, based on the frame period decided by the deciding unit, whether accumulation and reading out of electric charge not for use in an image generating process is set in the frame period; and a control unit adapted to control the sensor based on the determination by the determining unit.

16 Claims, 11 Drawing Sheets

PHOTOGRAPHING CONTROL APPARATUS AND METHOD

BACKGROUND OF THE INVENTION

1. Field of the Invention

The present invention relates to a photographing control apparatus and method.

2. Description of the Related Art

In recent years, there have been calls for a radiographic image photographing apparatus compatible with diverse photographic modes such as moving image photographing and energy subtraction photographing, rather than only still image photographing, with a single device configuration. A radiographic image photographing apparatus compatible with these diverse photographic modes is shown in Japanese Patent Laid-Open No. 2005-287773, for example.

Here, operations in a moving image photographing mode shown in Japanese Patent Laid-Open No. 2005-287773 will be described using FIGS. 7 and 8.

FIG. 7, showing a conventional example, is a timing chart showing exemplary timing for irradiating X-rays and for accumulating and reading out electric charge in a sensor in moving image photographing mode. In FIG. 7, timing is shown in the case where, in the frame period of a single frame, reading out of electric charge in photoelectric conversion devices of the sensor is performed once after X-ray irradiation and then once without X-ray irradiation being performed.

Note that the reading out once after X-ray irradiation and once without X-ray irradiation, as shown in FIG. 7, both involve the reading out of electric charge from all of the photoelectric conversion devices (all pixels) of the sensor. Consequently, in FIG. 7, these readout periods are the same length (Tr). The reading out after X-ray irradiation is for obtaining an X-ray image, while the reading out without X-ray irradiation is for performing offset correction.

In FIG. 7, the relation of the following equation (1) holds, where Tf10 is the frame period of a single frame of an X-ray image, Tr is the charge readout period, Tw11 is the charge accumulation period when X-ray irradiation is performed, and Tw12 is the charge accumulation period when X-ray irradiation is not performed. At this time, the frame period Tf10 of a single frame is equal to the X-ray irradiation cycle.

$$Tf10 = (Tw11 + Tr) + (Tw12 + Tr) \tag{1}$$

An offset correction value Vo10 can be calculated by the following equation (2), where Vx is the pixel value read out when X-ray irradiation is performed, Vf is the pixel value read out when X-ray irradiation is not performed, and Vo10 is the offset correction value.

$$Vo10 = Vx - Vf \tag{2}$$

Since the offset correction value is proportionate to the charge accumulation period, the following equation (3) desirably is satisfied to completely remove offset.

$$Tw11 = Tw12 \tag{3}$$

In this case, the charge accumulation period Tw11 can be calculated by the following equation (4), when equation (3) is substituted into equation (1).

$$Tw11 = Tf10/2 - Tr \tag{4}$$

Since the charge accumulation period Tw11 when X-ray irradiation is performed is greater than an X-ray irradiation period Tx, as shown in FIG. 7, the following equation (5) needs to be satisfied, where Tx is the X-ray irradiation period.

$$Tw11 > Tx \tag{5}$$

FIG. 8, showing a conventional example, is a timing chart showing exemplary timing for irradiating X-rays and for accumulating and reading out electric charge in a sensor in moving image photographing mode. In FIG. 8, timing is shown in the case where, in the frame period of a single frame, reading out of electric charge in photoelectric conversion devices of the sensor is performed once after X-ray irradiation and then three times without X-ray irradiation being performed.

In FIG. 8, Tf11 is the frame period of a single frame of an X-ray image, Tr is the charge readout period, Tw13 is the charge accumulation period when X-ray irradiation is performed, and Tw14 is the charge accumulation period when X-ray irradiation is not performed. At this time, to completely remove offset, the following equation (6) desirably is satisfied, with similar effect to equation (3).

$$Tw13 = Tw14 \tag{6}$$

Therefore, the frame period Tf11 of a single frame is given by the following equation (7).

$$Tf11 = k \cdot (Tw13 + Tr) \tag{7}$$

Note that k is a positive integer showing the number of times charge accumulation and readout is repeated in the frame period of a single frame, with k=4 in the case of FIG. 8, and k=2 in the case of FIG. 7.

In FIG. 8, an offset correction value Vo11 can be calculated by the following equation (8), where Vx is the pixel value read out when X-ray irradiation is performed, Vf1, Vf2 and Vf3 are the pixel values read out when X-ray irradiation is not performed, and Vo11 is the offset correction value.

$$Vo11 = Vx - Vfn \tag{8}$$

Note that n is an integer between 1 and k−1.

The charge accumulation period Tw13 when X-ray irradiation is performed can be calculated by the following equation (9), based on equation (7).

$$Tw13 = Tf11/k - Tr \tag{9}$$

Since the charge accumulation period Tw13 when X-ray irradiation is performed is greater than an X-ray irradiation period Tx, as shown in FIG. 8, the following equation (10) needs to be satisfied, where Tx is the X-ray irradiation period.

$$Tw13 > Tx \tag{10}$$

Here, equation (4) is included in equation (9), since a comparison of equations (4) and (9) shows that equation (4) is equivalent to equation (9) with k=2 substituted therein.

While Japanese Patent Laid-Open No. 2005-287773 shows the case where low voltage X-rays and high voltage X-rays are irradiated once each as an energy subtraction photographing mode, energy subtraction photographing of a moving image is possible if this process is repeated. Here, the operations in energy subtraction photographing mode for a moving image in this case will be described using FIGS. 9 and 10.

FIG. 9, showing a conventional example, is a timing chart showing exemplary timing for irradiating X-rays and for accumulating and reading out electric charge in photoelectric conversion devices of a sensor in energy subtraction photographing mode for a moving image. In FIG. 9, timing is shown in the case where, in the frame period of a single frame, reading out is performed once after low voltage X-ray irradiation, once after high voltage X-ray irradiation, and once without X-ray irradiation being performed.

In FIG. 9, the following equation (11) holds, where Tf12 is the frame period of a single frame of an X-ray image, Txl is the low voltage X-ray irradiation period, Txh is the high voltage X-ray irradiation period, Tw15 is the charge accumulation period when low voltage X-ray irradiation is performed, Tw16 is the charge accumulation period when high voltage X-ray irradiation is performed, and Tw17 is the charge accumulation period when X-ray irradiation is not performed.

$$Tfl2=(Tw15+Tr)+(Tw16+Tr)+(Tw17+Tr) \quad (11)$$

Offset correction values can be calculated by the following equation (12), where Vxl is the pixel value read out when low voltage X-ray irradiation is performed, Vxh is the pixel value read out when high voltage X-ray irradiation is performed, Vf is the pixel value read out when X-ray irradiation is not performed, Vol is the offset correction value when low voltage X-ray irradiation is performed, and Voh is the offset correction value when high voltage X-ray irradiation is performed.

$$Vol=Vxl-Vf, Voh=Vxh-Vf \quad (12)$$

To completely remove offset, the following equation (13) desirably is satisfied, with similar effect to equation (3).

$$Tw15=Tw16=Tw17 \quad (13)$$

The low voltage X-ray irradiation period Txl and the high voltage X-ray irradiation period Txh may differ, provided that equation (13) holds.

Consequently, the charge accumulation period Tw15 when low voltage X-ray irradiation is performed can be calculated by the following equation (14), when equation (13) is substituted into equation (11).

$$Tw15=Tfl2/3-Tr \quad (14)$$

Since the charge accumulation period Tw15 when low voltage X-ray irradiation is performed is greater than the low voltage X-ray irradiation period Txl and high voltage X-ray irradiation period Txh, the following equation (15) needs to be satisfied.

$$Tw15>Txl, Tw15>Txh \quad (15)$$

FIG. 10, showing a conventional example, is a timing chart showing exemplary timing for irradiating X-rays and for accumulating and reading out electric charge in photoelectric conversion devices of a sensor in energy subtraction photographing mode for a moving image. In FIG. 10, timing is shown in the case where, in the frame period of a single frame, reading out is performed once each after low voltage X-ray irradiation and without X-ray irradiation being performed, and once each after high voltage X-ray irradiation and without X-ray irradiation being performed.

In FIG. 10, the following equation (16) holds, where Tfl3 is the frame period of a single frame of an X-ray image, Txl is the low voltage X-ray irradiation period, Txh is the high voltage X-ray irradiation period, Tw18 is the charge accumulation period when low voltage X-ray irradiation is performed, Tw19 is the following charge accumulation period when X-ray irradiation is not performed, Tw20 is the charge accumulation period when high voltage X-ray irradiation is performed, and Tw21 is the following charge accumulation period when X-ray irradiation is not performed.

$$Tfl3=(Tw18+Tr)+(Tw19+Tr)+(Tw20+Tr)+(Tw21+Tr) \quad (16)$$

Offset correction values can be calculated by the following equation (17), where Vxl is the pixel value read out when low voltage X-ray irradiation is performed, Vf1 is the following pixel value read out when X-ray irradiation is not performed, Vxh is the pixel value read out when high voltage X-ray irradiation is performed, Vfh is the following pixel value read out when X-ray irradiation is not performed, Vol is the offset correction value when low voltage X-ray irradiation is performed, and Voh is the offset correction value when high voltage X-ray irradiation is performed.

$$Vol=Vxl-Vfl, Voh=Vxh-Vfh \quad (17)$$

To completely remove offset, the following equations (18) and (19) desirably are satisfied, with similar effect to equation (3).

$$Tw18=Tw19 \quad (18)$$

$$Tw20=Tw21 \quad (19)$$

At this time, the low voltage X-ray irradiation period Txl and the high voltage X-ray irradiation period Txh may differ, provided that equations (18) and (19) hold.

Consequently, the following equation (20) is given, when equations (18) and (19) are substituted into equation (16).

$$Tw18+Tw20=Tfl3/2-2Tr \quad (20)$$

Since the charge accumulation periods when X-ray irradiation is performed are greater than the X-ray irradiation periods, the following equation (21) needs to be satisfied.

$$Tw18>Txl, Tw20>Txh \quad (21)$$

Normally, the low voltage X-ray irradiation period Txl and high voltage X-ray irradiation period Txh are predetermined, often so that the following equations (22) and (23), for example, hold.

$$Tw18=Txl+\alpha \quad (22)$$

$$Tw20=Txh+\alpha \quad (23)$$

If the photographing frame rate is high (e.g., approx. 30 fps), α often takes a value of a few milliseconds.

When arranged using equations (20), (22) and (23), the charge accumulation period Tw18 when low voltage X-ray irradiation is performed is given by the following equation (24), and the charge accumulation period Tw20 when high voltage X-ray irradiation is performed is given by the following equation (25).

$$Tw18=Tfl3/4-Tr+(Txl-Txh)/2 \quad (24)$$

$$Tw20=Tfl3/4-Tr+(Txh-Txl)/2 \quad (25)$$

However, generally, with an X-ray photographing apparatus, photographing is performed at a reduced frame rate in order to lower the amount of radiation to which the subject (object) is exposed. There is a method that involves increasing the value of k in equation (7), for example, in the case where the frame rate is reduced, that is, in the case where photographing is performed with a longer frame period. Here, k=2 in FIG. 7, and k=4 in FIG. 8.

In the case of FIG. 8, the frame period Tfl1 of a single frame shown in FIG. 8 will be twice that of the frame period Tfl0 in FIG. 7, in order to satisfy the following equation (26).

$$Tw11=Tw12=Tw13=Tw14 \quad (26)$$

However, with the method that involves changing the value of k, the frame period Tfl1 of a single frame can only be lengthened in integer multiples of the frame period Tfl0 shown in FIG. 7. That is, it is difficult, in this case, to appropriately lower the frame rate in order to reduce the amount of radiation to which the subject (object) is exposed.

Another method in which photographing is performed with a longer frame period in order to reduce the amount of radiation to which the subject (object) is exposed involves lengthening the charge accumulation period. A timing chart thereof is shown in FIG. 11. FIG. 11, showing a conventional example, is a timing chart showing exemplary timing for irradiating X-rays and for accumulating and reading out electric charge in photoelectric devices of a sensor in moving image photographing mode. In FIG. 11, timing is shown in the case where k=2 and the charge accumulation period has been lengthened in comparison to the example in FIG. 7.

In FIG. 11, Tf14 is the frame period of a single frame of an X-ray image, Tr is the charge readout period, Tw31 is the charge accumulation period when X-ray irradiation is performed, and Tw32 is the charge accumulation period when X-ray irradiation is not performed.

Here, the relation of the following equation (27) holds if the frame period Tf14 of a single frame is greater than the frame period Tf10 in FIG. 7.

$$Tw31 > Tw11 \qquad (27)$$

However, the amount of dark current flowing to the photoelectric conversion devices of the sensor increases when the charge accumulation period is lengthened, as shown in FIG. 11, which increases the amount of electric charge that accumulates in the photoelectric conversion devices. The signal-to-noise (S/N) ratio deteriorates when the amount of accumulated charge increases, narrowing the dynamic range. The same problems similarly exist in relation to energy subtraction photographing mode and stereo photographing mode.

SUMMARY OF THE INVENTION

The present invention has been made in consideration of the foregoing problems, and has as its object to prevent deterioration of the S/N ratio of a radiographic image and to avoid narrowing of the dynamic range, even in the case where the amount of radiation to which an object is exposed is reduced by lowering the frame rate as necessary.

According to one aspect of the present invention, a photographing control apparatus that controls a sensor for accumulating and reading out electric charge in order to obtain an image, includes: a deciding unit adapted to decide a frame period showing an image photographing interval, based on an input of an input unit; a determining unit adapted to determine, based on the frame period decided by the deciding unit, whether accumulation and reading out of electric charge not for use in an image generating process is set in the frame period; and a control unit adapted to control the sensor based on the determination by the determining unit.

According to another aspect of the present invention, a control method of a photographing control apparatus that controls a sensor for accumulating and reading out electric charge in order to obtain an image, includes the steps of: deciding a frame period showing an image photographing interval, based on an input of an input unit; determining, based on the frame period decided by the deciding step, whether accumulation and reading out of electric charge not for use in an image generating process is set in the frame period; and controlling the sensor based on the determination in the determining step.

Further features of the present invention will become apparent from the following description of exemplary embodiments (with reference to the attached drawings).

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE EMBODIMENTS

Preferred embodiments of the present invention will be described in detail in accordance with the accompanying drawings.

Hereinafter, a first embodiment of the present invention will be described using the accompanying drawings.

Figure 1:
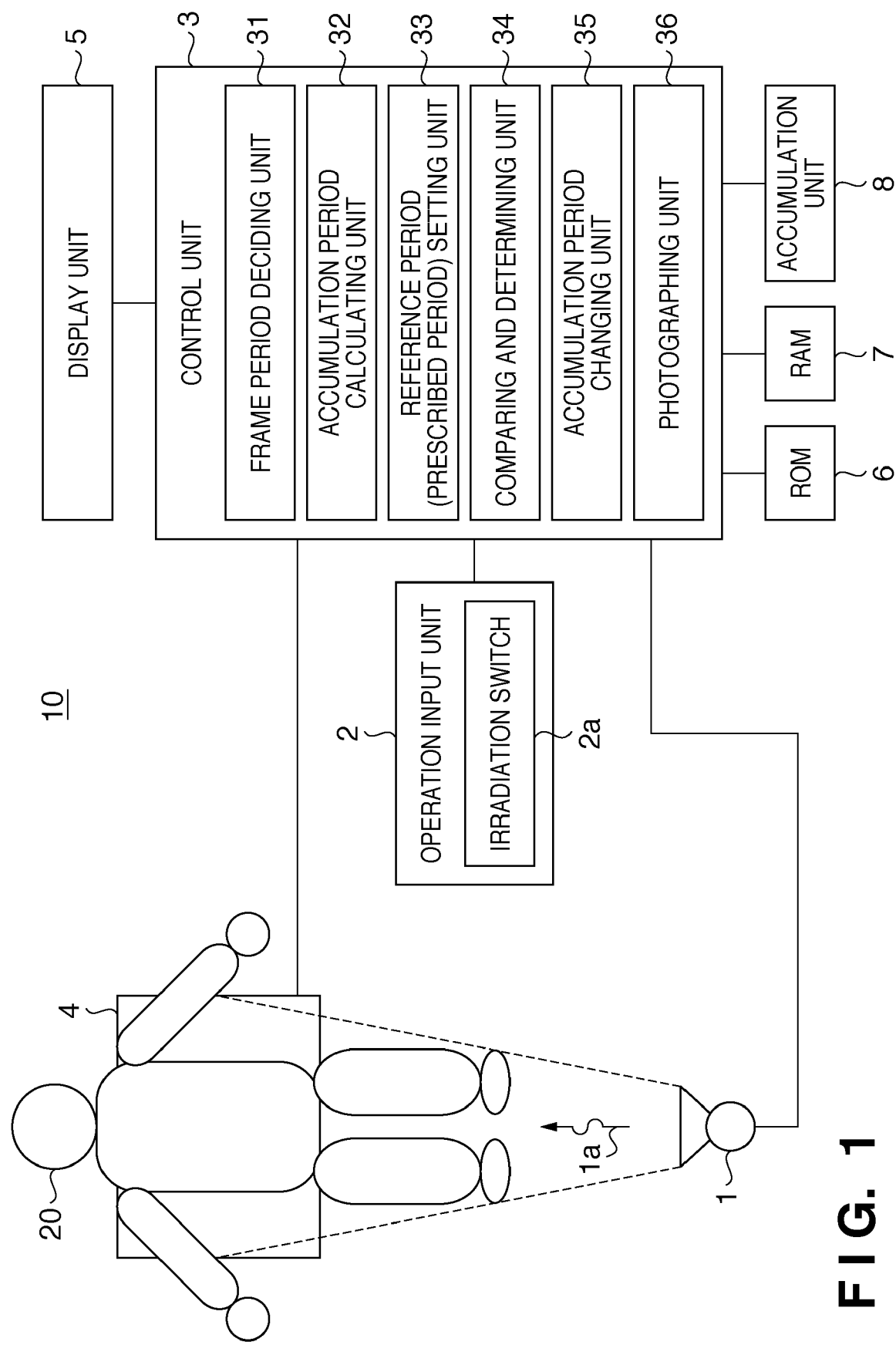
FIG. 1 is a block diagram showing an exemplary schematic configuration of an X-ray photographing apparatus (photographing control apparatus) according to a first embodiment of the present invention.

FIG. 1 is a block diagram showing an exemplary schematic configuration of an X-ray photographing apparatus (photographing control apparatus) according to the first embodiment of the present invention.

As shown in FIG. 1, the X-ray photographing apparatus 10 is constituted to have an X-ray generation unit 1, an operation input unit 2, a control unit 3, a sensor 4, a display unit 5, a ROM 6, a RAM 7, and an accumulation unit 8. A frame period deciding unit 31, an accumulation period calculating unit 32, a reference period (prescribed period) setting unit 33, a comparing and determining unit 34, an accumulation period changing unit 35, and a photographing unit 36 are included in the control unit 3 as functional elements.

The X-ray generation (radiation generation unit) unit 1 is able to continuously generate pulsed X-rays 1a with respect to an object (subject) 20, and is constituted by an X-ray tube, for example.

The operation input unit 2 is operated when a user performs an input instruction with respect to the X-ray photographing apparatus 10. This operation input unit 2 includes an irradiation switch 2a operated by the user when generating the X-rays 1a from the X-ray generation unit 1.

The control unit 3 reads out computer programs and the like stored in the ROM 6, for example, and is constituted by a CPU or the like that controls the entire X-ray photographing apparatus 10 based on the programs and the like. In the present embodiment, in particular, the control unit 3 realizes processing in the functional elements 31 to 36, based on programs and the like stored in the ROM 6.

Here, the frame period determining unit 31 decides a photographing interval (frame period) in X-ray image frames. The accumulation period calculating unit 32 calculates an accumulation period (first accumulation period) related to accumulation of electric charge, out of the accumulation and reading out of electric charge in the sensor 4 alternately performed repeatedly when obtaining the X-ray image of a single frame. The reference period setting unit 33 sets a reference period (prescribed period) constituting a reference. The comparing and determining unit 34 compares the first accumulation period and the reference period. The accumulation period changing unit 35 sets a dummy accumulation period and readout period in the frame period of a single frame and changes the first accumulation period to a second accumulation period that is shorter than the first accumulation period, if the first accumulation period is greater than the reference period. Here, a dummy accumulation period and readout period indicates the accumulation period and readout period of electric charge that is discarded without being used in an X-ray image generating process. The photographing unit 36 controls the sensor 4 based on the first accumulation period without setting dummy accumulation and readout periods, if it is determined by the comparing and determining unit 34 that the first accumulation period is less than or equal to the reference period. On the other hand, the photographing unit 36 controls the sensor 4 based on the second accumulation period, if it is determined by the comparing and determining unit 34 that the first accumulation period is greater than the reference period. Dummy accumulation and reading out is then performed. Note that the accumulation period calculating unit 32, the reference period setting unit 33, the comparing and determining unit 34, and the accumulation period changing unit 35 constituted a "determining unit". The photographing unit 36 constitutes a "control unit".

The sensor 4 detects X-rays 1a that have passed through the object 20 after being irradiated from the X-ray generation unit 1, under the control in the control unit 3.

In this sensor 4, pixels each including a photoelectric conversion device and TFT, for example, are arrayed two-dimensionally, in which case, phosphors, for example, are provided on the pixels. In this case, X-rays incident on the sensor 4 are converted to visible light by the phosphors, the resultant visible light is incident on the photoelectric conversion devices of the pixels, and electric charge is generated in the photoelectric conversion devices according to the visible light. Note that while "conversion elements" for converting incident X-rays to electric charge are constituted by the above phosphors and photoelectric conversion devices in the present embodiment, they may be constituted by so-called direct conversion type conversion elements that convert incident X-rays directly to electric charge without the provision of phosphors, for example. Consequently, in the following description, the sensor 4 will be described as having "conversion elements" two-dimensionally arrayed therein.

As described in Description of Related Art, the sensor 4 is able to capture an X-ray image by alternately accumulating and reading out the electric charge of the conversion elements repeatedly.

The display unit 5 displays X-ray images based on electric charge read out from the sensor 4, operation user interfaces (UIs) and the like, under the control of the control unit 3.

The ROM 6 stores computer programs and the like required in the processing shown below in FIG. 2 and other controls of the X-ray photographing apparatus 10 performed in the control unit 3, for example.

The RAM 7 is used when the control unit 3 performs various controls, for example, and temporarily stores various information calculated and processed by the control unit 3, and various information input by the user via the input unit 2, for example.

The accumulation unit 8 accumulates and stores the image data of X-ray images (radiographic images) based on X-rays detected by the sensor 4, for example.

In FIG. 1, the control unit 3 performs control so that pulsed X-rays 1a are irradiated from the X-ray generation unit 1, when the irradiation switch 2a is operated and turned on. The control unit 3 generates an X-ray image by reading out, from the sensor 4 in synchronous with the pulse of the X-rays 1a, electric charge based on X-rays 1a that have passed through the object (subject) 20, and displays the X-ray image on the display unit 5 after performing image processing thereon as necessary.

In the case where so-called pulse X-ray moving image photographing is performed by the X-ray photographing apparatus 10, the time interval for which the pulsed X-rays 1a are irradiated is determined using the frame period of a single frame determined by the frame period determining unit 31. The timing of accumulation and reading out of electric charge in the conversion elements of the sensor 4 is determined using the frame period deciding unit 31, the accumulation period calculating unit 32, the comparing and determining unit 34, and the accumulation period changing unit 35.

The control unit 3 (photographing unit 36) then performs pulse X-ray moving image photographing by controlling the sensor 4, based on the accumulation period of electric charge in the conversion elements determined by the accumulation period calculating unit 32 or the accumulation period changing unit 35.

Next, processing procedures of the X-ray photographing apparatus 10 according to the first embodiment will be described.

Figure 2:
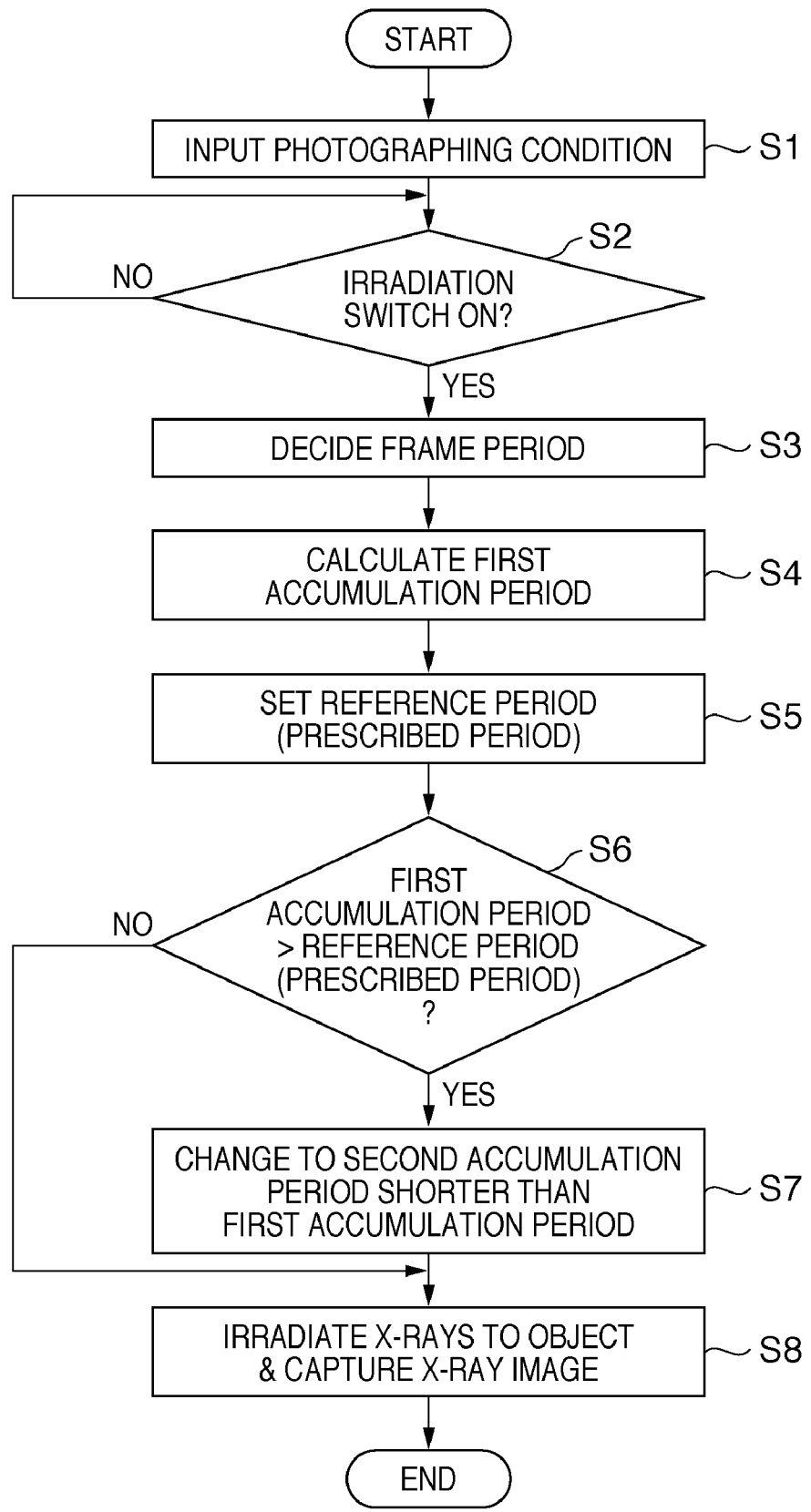
FIG. 2 is a flowchart showing exemplary processing procedures of the X-ray photographing apparatus (photographing control apparatus) according to the first embodiment of the present invention.

FIG. 2 is a flowchart showing exemplary processing procedures of the X-ray photographing apparatus (photographing control apparatus) according to the first embodiment of the present invention.

Firstly, in step S1, when photographing conditions are input by the user via the operation input unit 2, the control unit 3 detects this input, and stores and thereby sets the various information input via the operation input unit 2 in the RAM 7, for example. Here, in the present embodiment, it is assumed that values related to the frame rate Fr and k (k being a positive integer showing the repetitions of charge accumulation and reading out), an X-ray irradiation period Tx, and the like are input by the user as photographing conditions, and that this information is stored and thereby set in the RAM 7.

Next, in step S2, the control unit 3 determines whether the irradiation switch 2a has been operated by the user and turned on. If it is determined that the irradiation switch 2a is not on, the control unit 3 waits at step S2 until it is determined at step S2 that the irradiation switch 2a has been turned on.

On the other hand, if it is determined at step S2 that the irradiation switch 2a has been turned on, the processing proceeds to step S3. Note that step S2 may be provided between steps S7 and S8 described below. After proceeding to step S3, the frame period deciding unit 31 in the control unit 3 decides the photographing interval (frame period) in X-ray image frames, based on the frame rate set in step S1. The processing of step S3 will now be described in detail.

With X-ray image photographing in moving image photographing mode, the frame period of a single frame needs to be determined. Here, in the following description, an exemplary case where the frame period Tf10 of a single frame shown in FIG. 7 (or FIG. 3 discussed below) is determined will be described.

The frame period deciding unit 31 decides the frame period Tf10 of a single frame by calculating the following equation (28), using information on the frame rate Fr obtained in step S1.

$$Tf10 = 1/Fr \tag{28}$$

The frame period deciding unit 31 then stores and thereby sets information on the calculated frame period Tf10 of a single frame in the RAM 7, for example.

Next, in step S4, the accumulation period calculating unit 32 in the control unit 3 calculates a first accumulation period related to accumulation of electric charge, out of the accumulation and reading out of electric charge in the sensor 4 alternately performed repeatedly when obtaining an X-ray image of a single frame. The processing of step S4 will now be described in detailed.

In the first embodiment, accumulation and reading out of electric charge with X-ray irradiation is performed once and accumulation and reading out of electric charge without X-ray irradiation is repeated k−1 times in the frame period of a single frame, not including dummy accumulation and reading out of electric charge. That is, in the first embodiment, accumulation and reading out of electric charge is repeatedly performed a total of k times in the frame period of a single frame, not including dummy accumulation and reading out of electric charge. Note that in the following description, this will be described with the example shown in FIG. 7.

Figure 7:
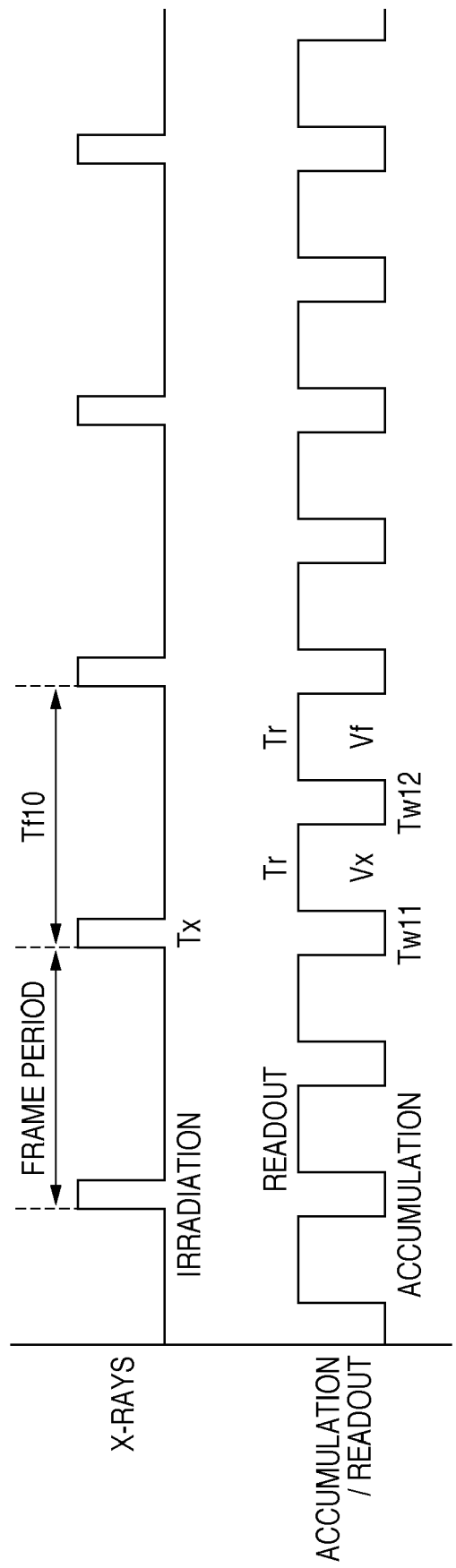
FIG. 7, showing a conventional example, is a timing chart showing exemplary timing for irradiating X-rays and for accumulating and reading out electric charge in a sensor in moving image photographing mode.

The accumulation period calculating unit 32 calculates, as the first accumulation period in the first embodiment, the charge accumulation period Tw11 with X-ray irradiation shown in FIG. 7, using the following equation (29) based on the above equation (9).

$$Tw11 = Tf10/k - Tr \tag{29}$$

Here, as described above, Tr shows the charge readout period and takes a constant value irrespective of the accumulation period. To completely remove offset, the charge accumulation periods Tw11 and Tw12 are made the same, as shown in equation (3). Consequently, the first accumulation period Tw11 of the present embodiment increases with increases in the frame period Tf10.

The accumulation period calculating unit 32 stores and thereby sets information on the computed first accumulation period Tw11 in the RAM 7, for example, as charge accumulation period information.

Next, in step S5, the reference period setting unit 33 in the control unit 3 sets a reference period (prescribed period) constituting a reference.

In the present embodiment, the reference period setting unit 33 sets a reference period (prescribed period) Tc given by the following equation (30), based on a value related to k obtained in step S1 and the X-ray irradiation period Tx.

$$Tc = Tx + Tr/k \tag{30}$$

The reference period setting unit 33 stores and thereby sets information on the computed reference period Tc in the RAM 7, for example.

Next, in step S6, the comparing and determining unit 34 in the control unit 3 compares the first accumulation period computed at step S4 with the reference period set at step S5, and determines whether the first accumulation period is greater than the reference period.

In the present embodiment, the comparing and determining unit 34 determines whether equation (31) shown below is satisfied.

$$Tw11 > Tc \tag{31}$$

Here, the following equation (32) holds when equation (30) is substituted into equation (31).

$$Tw11 > Tx + Tr/k \tag{32}$$

The following equation (33) holds when equation (29) is substituted into equation (32).

$$Tf10 > (k+1) \cdot Tr + k \cdot Tx \tag{33}$$

Consequently, equation (33) has the same significance as equation (32), and if equation (32) holds, then equation (33) also holds.

If equation (33) holds, dummy accumulation and reading out of electric charge can then be further inserted in the frame period (Tf10) of a single frame.

If it is determined in step S6 that the first accumulation period is greater than the reference period, the processing proceeds to step S7. Having proceeded to step S7, the accumulation period changing unit 35 in the control unit 3 sets a dummy accumulation period in the frame period of a single frame, and changes the first accumulation period to a second accumulation period that is shorter than the first accumulation period. The processing of step S7 will now be described in detail.

Figure 3:
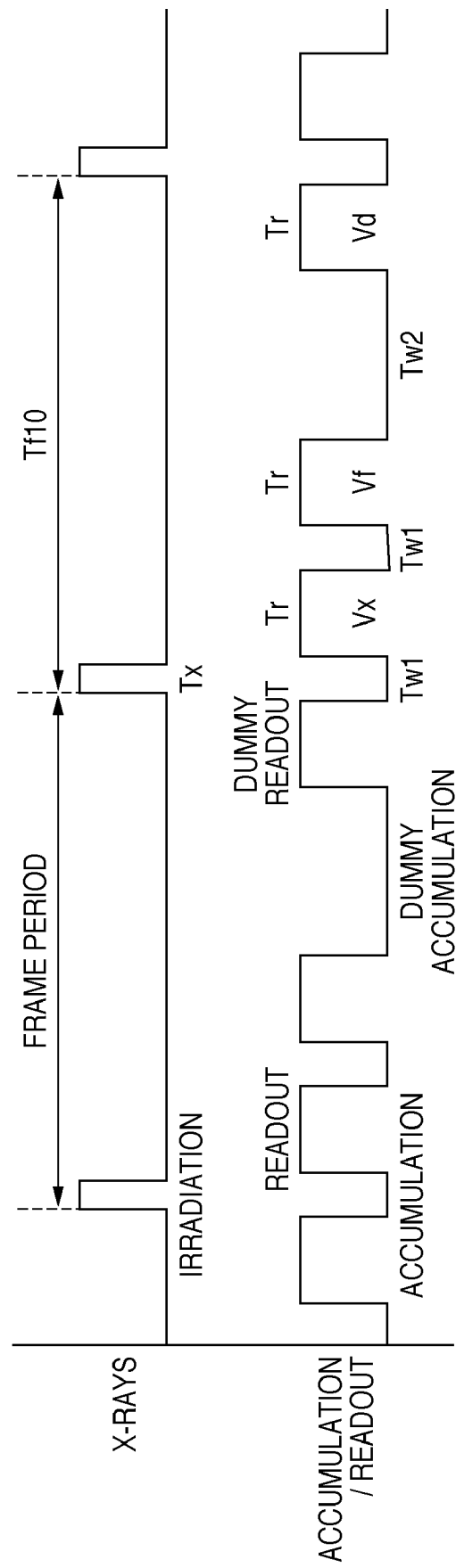
FIG. 3, showing exemplary operations of the X-ray photographing apparatus (photographing control apparatus) according to the first embodiment of the present invention, is a timing chart showing exemplary timing for irradiating X-rays and for accumulating and reading out electric charge in a sensor in moving image photographing mode.

FIG. 3, showing exemplary operations of the X-ray photographing apparatus (photographing control apparatus) according to the first embodiment of the present invention, is a timing chart showing exemplary timing for irradiating X-rays and for accumulating and reading out electric charge in a sensor in moving image photographing mode. In the timing chart of FIG. 3, k=2, and dummy accumulation and dummy reading out of electric charge in the sensor 4 has been added, in the frame period (Tf10) of a single frame, to FIG. 7 showing the conventional example. Here, in FIG. 3, the charge accumulation period when X-ray irradiation is performed and the charge accumulation period when X-ray irradiation is not performed are set to the same charge accumulation period Tw1, based on the effect of equation (3).

The accumulation period changing unit 35 sets a dummy accumulation period Tw2 as given in the following equation (34), where Tw1 is the second accumulation period, Tf10 is the frame period, and Tr is the charge readout period.

$$Tw2 = Tf10 - (k \cdot Tw1 + (k+1) \cdot Tr) \tag{34}$$

In this case, the second accumulation period Tw1 is set so that the following equation (35) is satisfied, using similar effect to the above the above equations (5) and (10).

$$Tw1 > Tx \quad (35)$$

Note that Tr is the dummy readout period. Also, the second accumulation period Tw1 is set as a shorter accumulation period than the first accumulation period (Tw11 shown in FIG. 7) by the accumulation period changing unit 35, and, in the present embodiment, is set as a period (specifically, reference period Tc, for example) less than or equal to the reference period Tc, for example. At this time, since the second accumulation period Tw1 is set so as to satisfy the above equation (35), in the case of the present embodiment, the second accumulation period Tw1 is set to be greater than the X-ray irradiation period Tx and less than or equal to the reference period Tc.

That is, in the present embodiment, if the first accumulation period Tw11 in FIG. 7 is greater than the reference period To, the dummy accumulation period Tw2 in FIG. 3 is set in the frame period of a single frame, and the first accumulation period Tw11 is changed to a second accumulation period Tw1 that is shorter than the first accumulation period.

Normally, the X-ray irradiation period Tx is a short constant period, enabling the second accumulation period Tw1 to be set to a short period. Therefore, as a result of equation (34), the dummy accumulation period Tw2 increases with increases in the frame period Tf10, without the second accumulation period Tw1 increasing. The frame period Tf10 can also be freely set by adjusting the dummy accumulation period Tw2. Note that offset correction values related to offset correction in the present embodiment can be calculated by equation (2), as described in the Description of the Related Art.

In the case where equation (31) holds and k=2 as shown in FIG. 3, equation (34) becomes the following equation (36).

$$Tw2 = Tf10 - (2Tw1 + 3Tr) \quad (36)$$

As described above, the charge accumulation period in the case where equation (31) does not hold can be calculated by equation (29), with the first accumulation period Tw11 increasing up to the reference period To with increases in the frame period Tf10 of a single frame.

Equation (31) will hold if the frame period Tf10 of a single frame increases further, in which case, the dummy accumulation period Tw2 is set, and the charge accumulation period is changed from the first accumulation period Tw11 to the shorter second accumulation period Tw1. The dummy accumulation period Tw2 shown in FIG. 3 can be calculated by the above equation (35).

Once the processing of step S7 is performed, the accumulation period changing unit 35 stores and thereby sets in the RAM 7, for example, as charge accumulation period information, information on the second accumulation period Tw1 and information on the dummy accumulation period Tw2, in place of information on first accumulation period Tw11.

Returning again to description of FIG. 2, if the processing of step S7 has ended or if the first accumulation period is determined not to be greater than the reference period in step S6, the processing proceeds to step S8.

Having proceeded to step S8, the photographing unit 36 in the control unit 3 performs an X-ray photographing process, based on the various information set at steps S1 and S3, and the charge accumulation period information set at step S4 or S7. The processing of step S8 will now be described in detail.

Firstly, the photographing unit 36 continuously irradiates pulsed X-rays 1a to the object (subject) 20 from the X-ray generation unit 1, based on the X-ray irradiation period Tx set at step S1 and the frame period Tf10 of a single frame set at step S3.

Next, the photographing unit 36 controls the accumulation of electric charge in the conversion elements of the sensor 4, based on the charge accumulation period information set in the RAM 7, and performs the X-ray photographing process.

The photographing unit 36 controls the sensor 4 at the charge accumulation and readout timing shown in FIG. 7, if information on the first accumulation period Tw11 is set as charge accumulation period information in the RAM 7, for example. The photographing unit 36 controls the sensor 4 at the charge accumulation and readout timing shown in FIG. 3, if information on the second accumulation period Tw1 and the dummy accumulation period Tw2 is set as charge accumulation period information in the RAM 7, for example.

Once the processing of step S8 is performed, the photographing unit 36 accumulates and stores, in the accumulation unit 8, for example, the image data of the X-ray image obtained as a result of the X-ray photographing process.

Note that in the first embodiment, a dummy accumulation and readout period is set if the first accumulation period is longer than a reference period. A dummy accumulation and readout period can thereby be provided directly, for example, rather than indirectly in the case where the frame period of a single frame is longer than a predetermined period. That is, an accumulation period TwX and a readout period TrX of electric charge for use in image processing are firstly set in this case. These periods are each slightly longer than X-ray irradiation period. The dummy accumulation period is then set to (frame period Tf11−2TwX−3TrX). If this is a negative time period, dummy accumulation and readout periods are not set.

In the first embodiment, the frame period determining unit 31 decides the frame period of a single frame by performing a calculation using equation (28), although the present invention is not limited to this embodiment. For example, the frame period deciding unit 31 may detect a frame period of a single frame directly input by the user via the operation input unit 2 in step S1, and decide on this frame period as the frame period of a single frame.

In the first embodiment, the constituent elements 31 to 36 are realized by software as a result in the control unit 3 running programs stored in the ROM 6, although these constituent elements may be realized by hardware, for example.

In the first embodiment, an example was described in which the order of driving was charge accumulation with X-ray irradiation, charge accumulation without X-ray irradiation, and dummy accumulation, as shown in FIG. 3, although the order of drive timing is not limited to this example. For example, the order of driving may be charge accumulation without X-ray irradiation, charge accumulation with X-ray irradiation, and dummy accumulation.

Second Embodiment

Hereinafter, a second embodiment of the present invention will be described using the accompanying drawings.

Here, the schematic configuration of an X-ray photographing apparatus (photographing control apparatus) according to the second embodiment is similar to the schematic configuration of the X-ray photographing apparatus 10 according to the first embodiment shown in FIG. 1.

Figure 4:
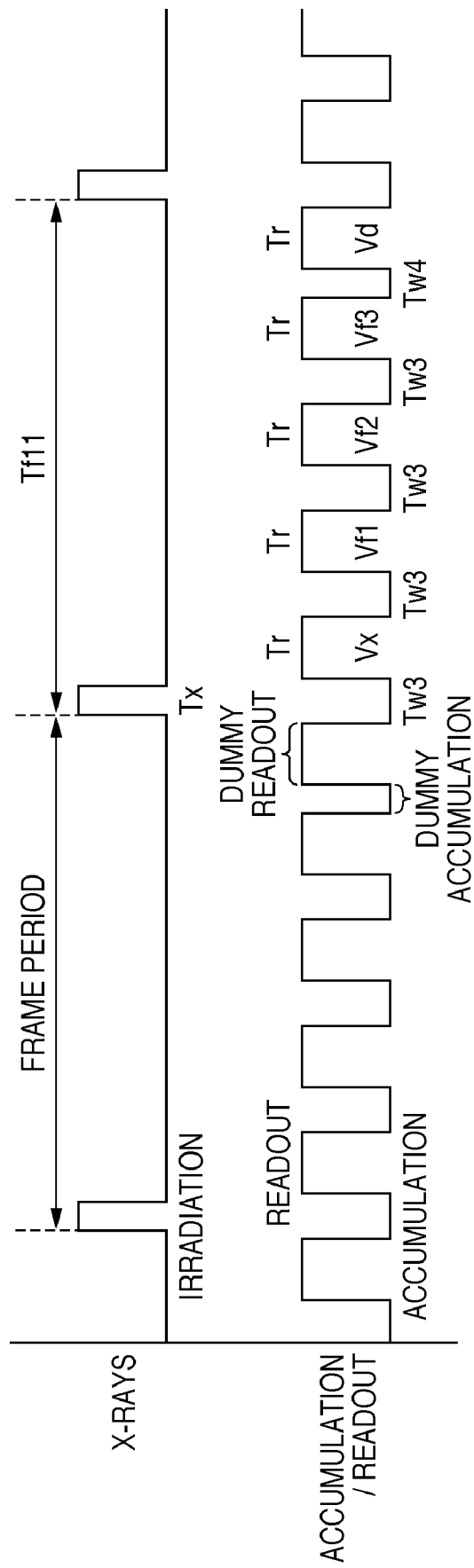
FIG. 4, showing exemplary operations of the X-ray photographing apparatus (photographing control apparatus) according to a second embodiment of the present invention, is a timing chart showing exemplary timing for irradiating X-rays and for accumulating and reading out electric charge in a sensor in moving image photographing mode.
Figure 8:
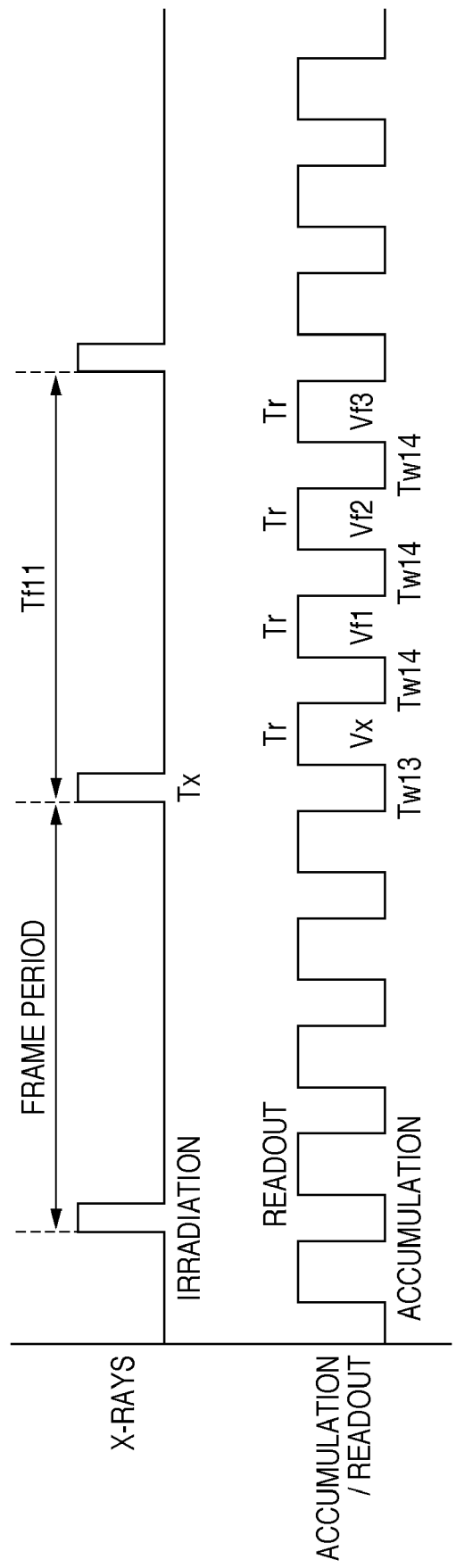
FIG. 8, showing a conventional example, is a timing chart showing exemplary timing for irradiating X-rays and for accumulating and reading out electric charge in a sensor in moving image photographing mode.

FIG. 4, showing exemplary operations of the X-ray photographing apparatus (photographing control apparatus) according to the second embodiment of the present invention, is a timing chart showing exemplary timing for irradiating X-rays and for accumulating and reading out electric charge in a sensor in moving image photographing mode. In the timing chart of FIG. 4, k=4, and dummy accumulation and dummy reading out of electric charge in the sensor 4 has been added, in the frame period (Tf11) of a single frame, to FIG. 8 showing the conventional example. Here, in FIG. 4, the charge accumulation period when X-ray irradiation is performed and the charge accumulation period when X-ray irradiation is not performed are set to the same charge accumulation period Tw3, based on the effect of equation (6).

That is, FIG. 4 shows the case where accumulation and reading out of electric charge with X-ray irradiation is performed once, and accumulation and reading out of electric charge without X-ray irradiation is performed three times for a total of four repetitions in the frame period of a single frame, not including dummy accumulation and reading out of electric charge.

In the case of the second embodiment, the charge accumulation period Tw13 with X-ray irradiation shown in FIG. 8 is applied as the first accumulation period.

In the case of the second embodiment, if Tw13>Tc holds based on equation (31), dummy accumulation and reading out of electric charge can be further inserted in the frame period (Tf11) of a single frame. In this case, the accumulation period changing unit 35 in the control unit 3 sets the dummy accumulation period Tw4 shown in FIG. 4 in the frame period (Tf11) of a single frame, and changes the first accumulation period Tw13 to a second accumulation period Tw3 that is shorter than the first accumulation period.

The dummy accumulation period Tw4 is given by the following equation (37), where k=4 as shown in FIG. 4, and Tw4 replaces Tw2 as the dummy accumulation period, Tf11 replaces Tf10 as the frame period, and Tw3 replaces Tw1 as the second accumulation period in equation (34).

$$Tw4=Tf11-(4Tw3+5Tr) \quad (37)$$

Offset correction values related to offset correction in the present embodiment can be calculated by equation (8), as described in the Description of the Related Art.

Third Embodiment

Hereinafter, a third embodiment of the present invention will be described using the accompanying drawings.

Here, the schematic configuration of an X-ray photographing apparatus (photographing control apparatus) according to the third embodiment is similar to the schematic configuration of the X-ray photographing apparatus 10 according to the first embodiment shown in FIG. 1.

Figure 9:
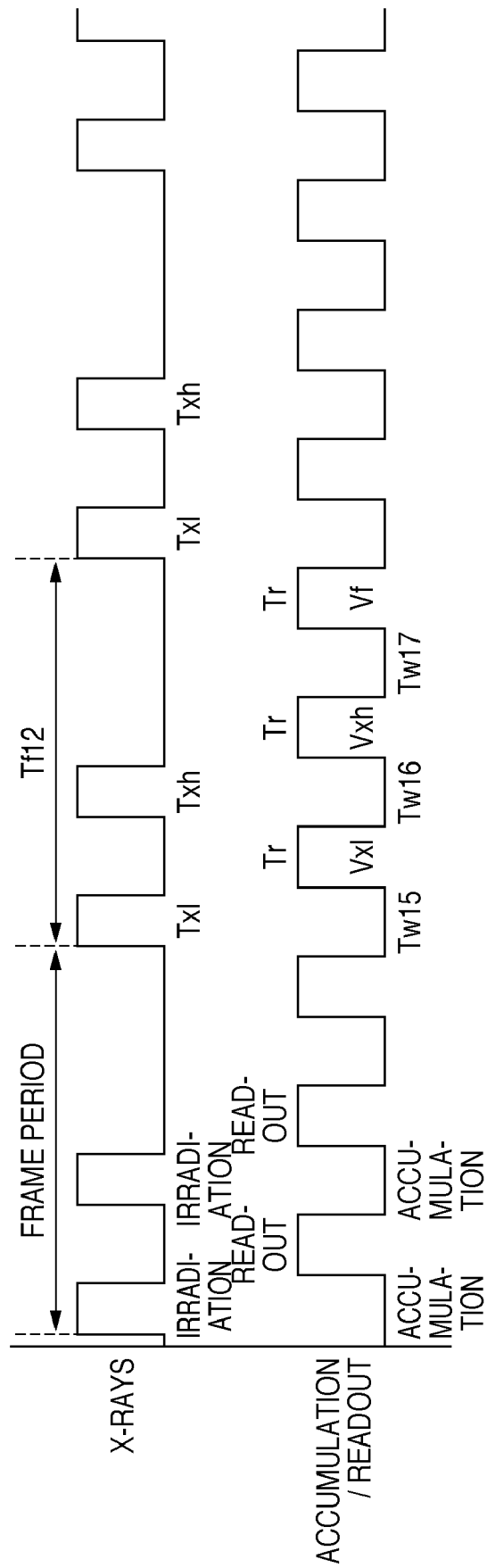
FIG. 9, showing a conventional example, is a timing chart showing exemplary timing for irradiating X-rays and for accumulating and reading out electric charge in photoelectric conversion devices of a sensor in energy subtraction photographing mode for a moving image.

The third embodiment corresponds to the moving image photographing mode shown in FIG. 9 of the conventional example. That is, in this embodiment, energy subtraction photographing is performed in which in the frame period of a single frame, reading out after low voltage X-ray irradiation is performed once, then reading out after high voltage X-ray irradiation is performed once, and reading out without X-ray irradiation is performed once.

With the X-ray photographing apparatus 10 according to the third embodiment, X-rays (first radiation) when the voltage of the X-ray generation unit 1 is low and X-rays (second radiation) when the voltage of the X-ray generation unit 1 is high are respectively pulse irradiated once every frame from the X-ray generation unit 1, under the control of the control unit 3.

In this case, the frame period determining unit 31 then determines the frame period Tf12 of a single frame in the third embodiment, with Tf12 shown in FIG. 9 replacing Tf10 as the frame period of a single frame in equation (28). The accumulation period calculating unit 32 calculates an accumulation period Tw15 when low voltage X-ray irradiation is performed as the first accumulation period, using the above equation (14). In this case, equation (15) needs to hold.

The reference period setting unit 33 sets the reference period Tc using the following equation (38).

$$Tc=Tx+Tr/3 \quad (38)$$

The comparing and determining unit 34 then determines whether equation (39) shown below is satisfied by comparing the first accumulation period Tw15 with the reference period Tc.

$$Tw15>Tc \quad (39)$$

Here, the following equation (40) holds when equation (38) is substituted into equation (39).

$$Tw15>Tx+Tr/3 \quad (40)$$

Equation (40) becomes the following equation (41), in view of equation (14).

$$Tf12>4Tr+3Tx \quad (41)$$

This equation (41) has the same significance as equation (40), so if equation (40) holds, equation (41) also holds.

If equation (40) holds, dummy accumulation and reading out of electric charge can be further inserted in the frame period (Tf12) of a single frame.

Figure 5:
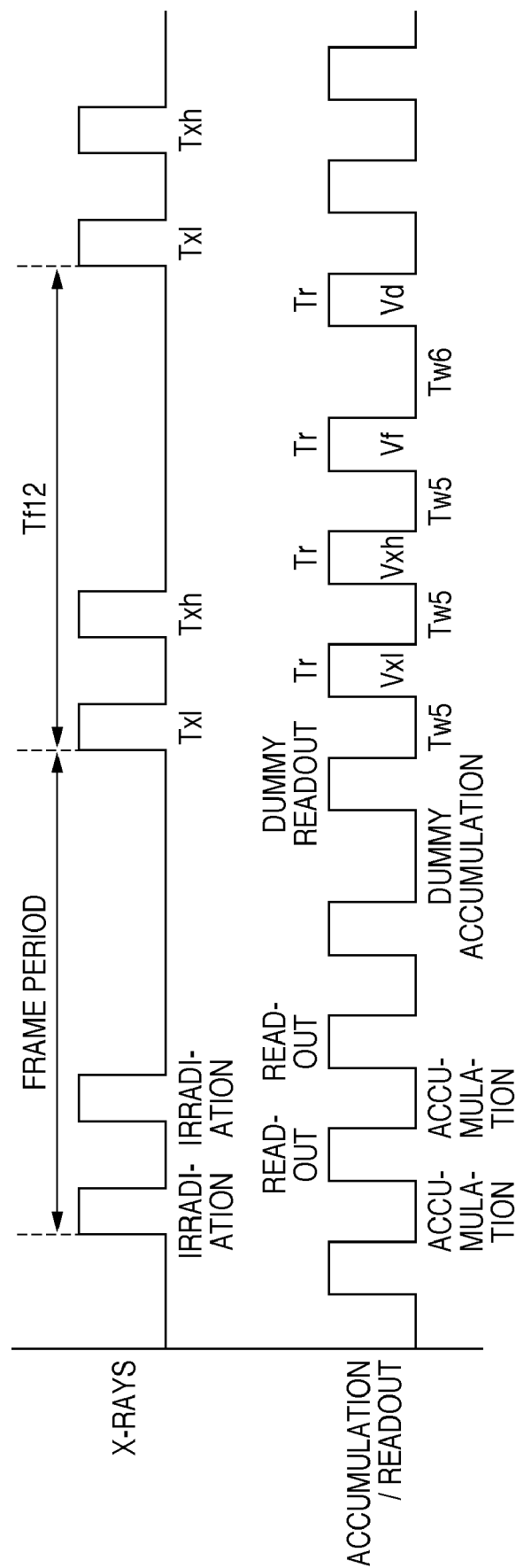
FIG. 5, showing exemplary operations of the X-ray photographing apparatus (photographing control apparatus) according to a third embodiment of the present invention, is a timing chart showing exemplary timing for irradiating X-rays and for accumulating and reading out electric charge in a sensor in moving image photographing mode.

FIG. 5, showing exemplary operations of the X-ray photographing apparatus (photographing control apparatus) according to the third embodiment of the present invention, is a timing chart showing exemplary timing for irradiating X-rays and for accumulating and reading out electric charge in a sensor in moving image photographing mode. In the timing chart of FIG. 5, dummy accumulation and dummy reading out of electric charge in the sensor 4 has been added, in the frame period (Tf12) of a single frame, to FIG. 9 showing the conventional example. Here, in FIG. 5, the charge accumulation period when X-ray irradiation is performed and the charge accumulation period when X-ray irradiation is not performed are set to the same charge accumulation period Tw5, based on the effect of equation (6).

The accumulation period changing unit 35 sets the dummy accumulation period Tw6 shown in FIG. 5 in the frame period (Tf12) of a single frame, and changes the first accumulation period Tw15 to a second accumulation period Tw5 that is shorter than the first accumulation period, if equation (39) holds.

In this case, the accumulation period changing unit 35 sets the dummy accumulation period Tw6 using the following equation (42), where Tr is the charge readout period.

$$Tw6=Tf12-(2Tw5+3Tr) \quad (42)$$

Since the second accumulation period Tw5 is greater than the X-ray irradiation periods Txl and Txh, the following equation (43) needs to be satisfied, using similar effect to equation (15).

$$Tw5>Txl, Tw5>Txh \quad (43)$$

If the X-ray irradiation periods Txl and Txh are the same period Tx, equation (43) can be represented as Tw5>Tx.

The second accumulation period Tw5 is set as a shorter accumulation period than the first accumulation period (Tw15 shown in FIG. 9) by the accumulation period changing unit 35, and, similarly to the first embodiment, is set as a period (specifically, reference period Tc, for example) less than or equal to the reference period Tc, for example. At this time, since the second accumulation period Tw5 is set so as to satisfy the above equation (43), in the case of the present embodiment, the second accumulation period Tw5 is set to be greater than the X-ray irradiation periods Txl and Txh, and less than or equal to the reference period Tc.

Normally, the X-ray irradiation periods Txl and Txh are short constant periods, enabling the second accumulation period Tw5 to be set to a short period. Therefore, as a result of equation (42), the dummy accumulation period Tw6 increases with increases in the frame period Tf12, without the second accumulation period Tw5 increasing. The frame period Tf12 can also be freely set by adjusting the dummy accumulation period Tw6. Note that offset correction values related to offset correction in the present embodiment can be calculated by equation (12), as described in the Description of the Related Art.

The charge accumulation period in the case where equation (39) does not hold can be calculated with equation (14). Equation (39) will hold if the frame period Tf12 of a single frame increases, in which case, the dummy accumulation period Tw6 is set, and the charge accumulation period is changed from the first accumulation period Tw15 to the shorter second accumulation period Tw5. In the case where the frame period Tf12 is further increased, the dummy accumulation period Tw6 increases.

In the third embodiment, an example was described in which the order of driving was accumulation with X-ray irradiation related to low voltage, accumulation with X-ray irradiation related to high voltage, accumulation without X-ray irradiation, and dummy accumulation, as shown in FIG. 5, although the order of drive timing is not limited to this example. For example, the order of driving may be accumulation with X-ray irradiation related to high voltage, accumulation with X-ray irradiation related to low voltage, accumulation without X-ray irradiation, and dummy accumulation.

Also, the X-ray generation unit 1 may be constituted by two (left and right) X-ray tubes, for example, and X-ray irradiation may be performed from one of the X-ray tubes (e.g., left) in place of low voltage X-ray irradiation, and X-ray irradiation may be performed from the other X-ray tube (e.g., right) in place of high voltage X-ray irradiation. Stereo photographing of moving images can thereby be performed with the same timing chart as FIG. 5.

Fourth Embodiment

Hereinafter, a fourth embodiment of the present invention will be described using the accompanying drawings. Here, the schematic configuration of an X-ray photographing apparatus (photographing control apparatus) according to the fourth embodiment is similar to the schematic configuration of the X-ray photographing apparatus 10 according to the first embodiment shown in FIG. 1.

Figure 10:
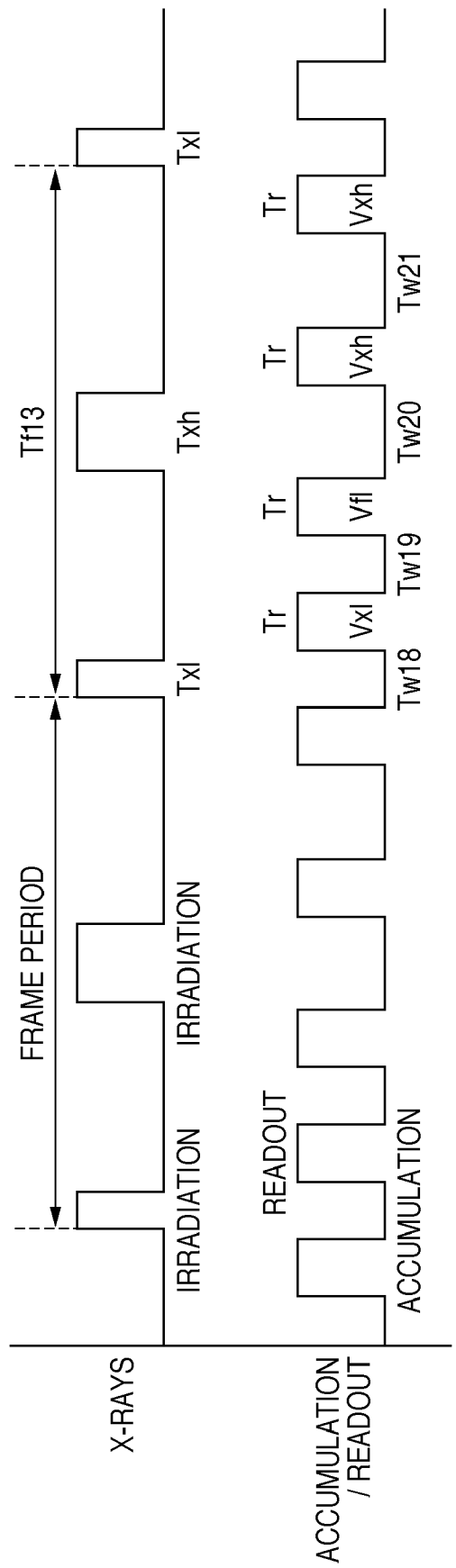
FIG. 10, showing a conventional example, is a timing chart showing exemplary timing for irradiating X-rays and for accumulating and reading out electric charge in photoelectric conversion devices of a sensor in energy subtraction photographing mode for a moving image.
Figure 11:
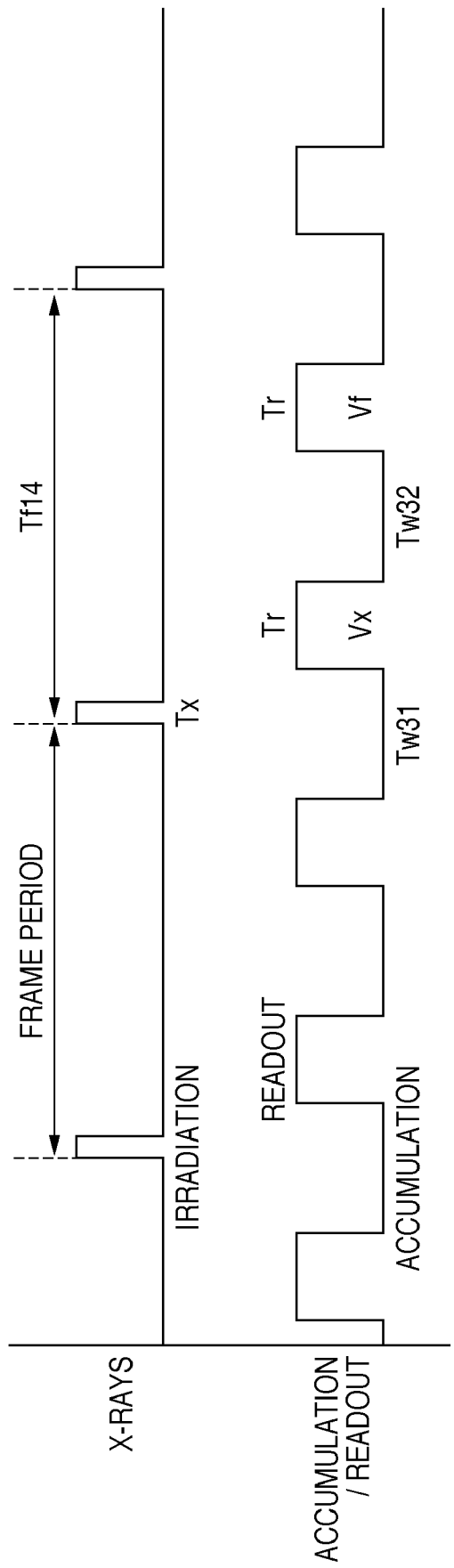
FIG. 11, showing a conventional example, is a timing chart showing exemplary timing for irradiating X-rays and for accumulating and reading out electric charge in photoelectric devices of a sensor in moving image photographing mode.

The fourth embodiment corresponds to the moving image photographing mode shown in FIG. 10 of the conventional example. That is, in this embodiment, energy subtraction photographing is performed in which in the frame period of a single frame, reading out after low voltage X-ray irradiation and without X-ray irradiation are each performed once, and then reading out after high voltage X-ray irradiation and without X-ray irradiation are each performed once.

With the X-ray photographing apparatus 10 according to the fourth embodiment, X-rays (first radiation) when the voltage of the X-ray generation unit 1 is low and X-rays (second radiation) when the voltage of the X-ray generation unit 1 is high are respectively pulse irradiated once every frame from the X-ray generation unit 1, under the control of the control unit 3.

In this case, the frame period deciding unit 31 then determines the frame period Tf13 of a single frame in the fourth embodiment, with Tf13 shown in FIG. 10 replacing Tf10 as the frame period of a single frame in equation (28). The accumulation period calculating unit 32 calculates an accumulation period Tw18 when low voltage X-ray irradiation is performed and an accumulation period Tw20 when high voltage X-ray irradiation is performed as the first accumulation period, using the above equations (24) and (25). In this case, equation (21) needs to hold.

The reference period setting unit 33 respectively sets reference periods Tc1 and Tc2 in the charge accumulation periods Tw18 and Tw20, using the following equations (44) and (45), where Txl is the low voltage X-ray irradiation period and Txh is the high voltage X-ray irradiation period.

$$Tc1 = Txl + Tr/4 \tag{44}$$

$$Tc2 = Txh + Tr/4 \tag{45}$$

The comparing and determining unit 34 then determines whether equations (46) and (47) shown below are satisfied.

$$Tw18 > Tc1 \tag{46}$$

$$Tw20 > Tc2 \tag{47}$$

In this case, the following equations (48) and (49) are given when equation (44) is substituted into equation (46) and equation (45) is substituted into equation (47).

$$Tw18 > Txl + Tr/4 \tag{48}$$

$$Tw20 > Txh + Tr/4 \tag{49}$$

At this time, the equations (48) and (49) can be rewritten as the following equation (50), in view of equations (24) and (25).

$$Tf13 > 5Tr + 2(Txl + Txh) \tag{50}$$

This equation (50) has the same significance as equations (48) and (49), so if equation (50) holds, equations (48) and (49) also hold.

If equation (50) holds, dummy accumulation and reading out of electric charge can be further inserted in the frame period (Tf13) of a single frame.

Figure 6:
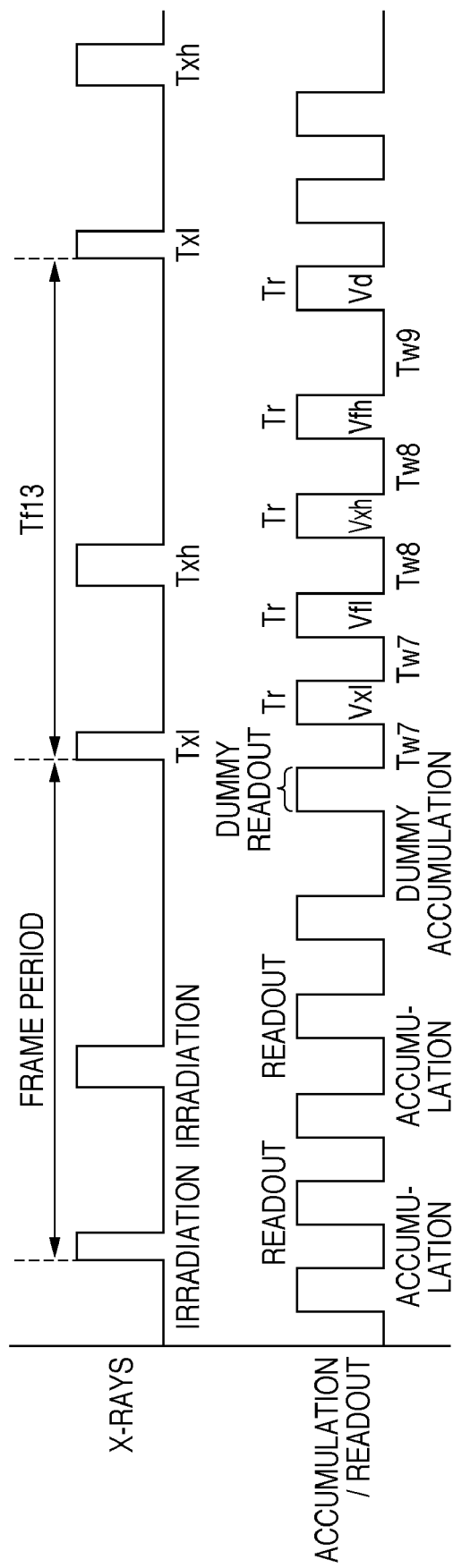
FIG. 6, showing exemplary operations of the X-ray photographing apparatus (photographing control apparatus) according to a fourth embodiment of the present invention, is a timing chart showing exemplary timing for irradiating X-rays and for accumulating and reading out electric charge in a sensor in moving image photographing mode.

FIG. 6, showing exemplary operations of the X-ray photographing apparatus (photographing control apparatus) according to the fourth embodiment of the present invention, is a timing chart showing exemplary timing for irradiating X-rays and for accumulating and reading out electric charge in a sensor in moving image photographing mode. In the timing chart of FIG. 6, dummy accumulation and dummy reading out of electric charge in the sensor 4 has been added, in the frame period (Tf13) of a single frame, to FIG. 10 showing the conventional example. Here, in FIG. 6, the charge accumulation period when low voltage X-ray irradiation is performed and the following charge accumulation period when X-ray irradiation is not performed are set to the same charge accumulation period Tw7, based on the effect of equation (18). Similarly, the charge accumulation period when high voltage X-ray irradiation is performed and the following charge accumulation period when X-ray irradiation is not performed are set to the same charge accumulation period Tw8, based on the effect of equation (19).

The accumulation period changing unit 35 sets the dummy accumulation period Tw9 shown in FIG. 5 in the frame period (Tf13) of a single frame, if equation (50) holds. The accumulation period changing unit 35 then changes the first accumulation period Tw18 to a second accumulation period Tw7 that is shorter than the first accumulation period Tw18, and changes the first accumulation period Tw20 to a second accumulation period Tw8 that is shorter than the first accumulation period Tw20.

In this case, the accumulation period changing unit 35 sets the dummy accumulation period Tw9 using the following equation (51), where Tr is the charge readout period.

$$Tw9=Tf13-(2\cdot(Tw7+Tw8)+5Tr) \quad (51)$$

At this time, since the second accumulation periods Tw7 and Tw8 are respectively longer than the X-ray irradiation periods Txl and Txh, the following equation (52) needs to be satisfied, using similar effect to equation (21).

$$Tw7>Txl, Tw8>Txh \quad (52)$$

Normally, the X-ray irradiation periods are short periods, enabling the second accumulation periods Tw7 and Tw8 to be set to short periods. Therefore, as a result of equation (51), the dummy accumulation period Tw9 increases with increases in the frame period Tf13, without the second accumulation periods Tw7 and Tw8 increasing. The frame period Tf13 can also be freely set by adjusting the dummy accumulation period Tw9. Note that offset correction values related to offset correction in the present embodiment can be calculated by equation (17), as described in the Description of the Related Art.

The charge accumulation periods in the case where equation (50) does not hold can be calculated by equations (24) and (25). Equation (50) will hold if the frame period Tf13 of a single frame increases, in which case, the dummy accumulation period Tw9 is set, and the charge accumulation periods are changed respectively from the first accumulation periods Tw18 and Tw20 to the shorter second accumulation periods Tw7 and Tw8. In the case where the frame period Tf13 is further increased, the dummy accumulation period Tw9 increases.

Next, the operation and effect of the present invention will be described in detail, taking the first embodiment as an example.

In FIG. 3, pixel values Vx are obtained from reading out electric charge when X-ray irradiation is performed, with the reading out being performed in order to obtain an X-ray image. At this time, pixel values proportionate to the intensity of the X-rays would be obtained as the pixel values Vx with an ideal sensor 4. However, in reality, offset values and noise are present in the pixel values Vx.

Here, focusing on a single arbitrary pixel of the sensor 4, the pixel value Vx of the arbitrary pixel of the sensor 4 is generally represented by the following equation (53), where X is the X-ray intensity, Vo is the offset value, and Vn1 is the value resulting from noise (noise value).

$$Vx=a\cdot X+Vo+Vn1 \text{ (a is a proportional constant)} \quad (53)$$

At this time, the offset value Vo increases in proportion to the charge accumulation period and differs slightly from pixel to pixel. The noise value Vn1 changes randomly within the range represented by the following equation (54).

$$-Vr1 \leq Vn1 \leq Vr1 \quad (54)$$

Here, Vr1 increases in proportion to the charge accumulation period.

Consequently, a clear X-ray image is not obtained since the pixel values Vx obtained by the reading out of electric charge when X-ray irradiation is performed also contains offset and noise values, despite being proportionate to the X-ray intensity.

In view of this, reading out of electric charge without X-ray irradiation is performed. Pixel values Vf are obtained with this reading out of electric charge when X-ray irradiation is not performed. With this reading out of electric charge when X-ray irradiation is not performed, offset and noise values are obtained, since reading out is performed without X-rays being irradiated. The pixel value Vf of a single arbitrary pixel of the sensor 4 is generally represented by the following equation (55), where Vo is the offset value obtained by the reading out of electric charge when X-ray irradiation is not performed, and Vn2 is the noise value.

$$Vf=Vo+Vn2 \quad (55)$$

At this time, the noise value Vn2 changes randomly within the range represented by the following equation (56).

$$-Vr2 \leq Vn2 \leq Vr2 \quad (56)$$

Here, Vr2 increases in proportion to the charge accumulation period.

A pixel value V from which the offset value Vo has been eliminated is obtained using the following equation (57), based on equations (53) and (55).

$$V=Vx-Vf=a\cdot X+Vn1-Vn2 \quad (57)$$

With the offset correction process, the above processing is performed per pixel on all of the pixels in the sensor 4. That is, the offset values Vo are removed from the pixel values Vx related to an X-ray image by reading out electric charge when X-ray irradiation is not performed. In this case, because the offset values Vo increase in proportion to the charge accumulation period, the charge accumulation period when X-ray irradiation is performed and the charge accumulation period when X-ray irradiation is not performed need to be substantially the same.

In the first embodiment, the dummy accumulation period Tw2 shown in FIG. 3 in the frame period (Tf10) of a single frame is set, and the accumulation period is changed from the first accumulation period Tw11 shown in FIG. 7 to the second accumulation period Tw1 shown in FIG. 3.

Firstly, being able to prevent deterioration of the S/N ratio of a radiographic image, that is, being able to improve the S/N ratio relative to the conventional example, will be discussed.

A term (Vn1−Vn2) of the noise value is included in the equation (57), and this noise value tends to increase as the charge accumulation period becomes longer, given equations (54) and (56). Therefore, the charge accumulation period becomes longer when the frame period (Tf10) increases, that is, when the frame rate decreases, and the noise value increases as a result. To prevent this, the charge accumulation periods when X-ray irradiation is performed and when X-ray irradiation is not performed are shortened by adding dummy reading out of electric charge, enabling the noise value to be reduced as a result. Thereby, deterioration of the S/N ratio of a radiographic image can be prevented, that is, the S/N ratio relative to the conventional example can be improved.

Next, being able to avoid narrowing of the dynamic range, that is, being able to widen the dynamic range relative to the conventional example will be discussed.

A term of the offset value Vo is present in the equation (53), and this offset value Vo increases in proportion to the charge accumulation period. Therefore, the charge accumulation period becomes longer when the frame period (Tf10) increases, that is, when the frame rate decreases, and the offset value Vo increases as a result. To prevent this, the charge accumulation periods when X-ray irradiation is performed and when X-ray irradiation is not performed are shortened by adding dummy reading out of electric charge, reducing the offset value Vo. As a result, narrowing of the dynamic range can be avoided, that is, the dynamic range can be widened relative to the conventional example.

The constituent elements of FIG. 1 constituting the X-ray photographing apparatus 10 according to the foregoing embodiments, as well as the steps of FIG. 2 showing a control method of the X-ray photographing apparatus, can be realized by the operation of a computer program stored in the ROM 6. This program and a computer-readable storage medium storing the program are included in the present invention.

Specifically, the program is provided to a computer by being recorded to a storage medium such as a CD-ROM, for example, or via a variety of transmission media. Apart from a CD-ROM, storage media that can be used for supplying the program include flexible disk, hard disk, magnetic tape, magneto-optical disk, and nonvolatile memory card. On the other hand, transmission media that can be used include communication media in a computer network (LAN, WAN such as the Internet, wireless communication network, etc.) system for supplying program information propagated as a propagating wave. Such communication media include cable lines such as optical fiber or wireless lines.

The functions of the X-ray photographing apparatus 10 according to the embodiments are not only realized by running a program provided to a computer. In the case where the functions of the X-ray photographing apparatus 10 according to the embodiments are realized in conjunction with an operating system (OS) or another application or the like being run on a computer by the program, that program is included in the present invention. Also, in the case where the functions of the X-ray photographing apparatus 10 according to the embodiments are realized by all or part of the processing of the supplied program being performed using the function expansion board or function expansion unit of a computer, that program is included in the present invention.

The foregoing embodiments merely illustrate specific examples for implementing the invention, and the technical scope of the invention is not to be construed restrictively as a result of these embodiments. That is, the invention can be implemented in various forms without departing from the technical idea or main features thereof.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-179893, filed on Jul. 9, 2007, which is hereby incorporated by reference herein in its entirety.

What is claimed is:

1. A photographing control apparatus that controls a sensor for accumulating and reading out electric charge in order to obtain an image, comprising:
   a deciding unit adapted to decide a frame period showing an image photographing interval, based on an input of an input unit;
   a determining unit adapted to determine, based on the frame period decided by the deciding unit, whether accumulation and reading out of electric charge not for use in an image generating process is set in the frame period; and
   a control unit adapted to control the sensor based on the determination by the determining unit.

2. The photographing control apparatus according to claim 1, wherein the determining unit includes:
   a calculating unit adapted to calculate a first accumulation period during which electric charge for obtaining the image is accumulated, based on the frame period decided by the deciding unit;
   a comparing unit adapted to compare the first accumulation period with a reference period constituting a reference; and
   a changing unit adapted to set accumulation and reading out of electric charge not for use in the image generating process, and change the first accumulation period to a second accumulation period that is shorter than the first accumulation period, if it is determined by the comparing unit that the first accumulation period is greater than the reference period.

3. The photographing control apparatus according to claim 2, wherein the first accumulation period is a charge accumulation period for when accumulation and reading out of electric charge are alternately performed repeatedly.

4. The photographing control apparatus according to claim 3, wherein
   the sensor detects irradiated radiation as electric charge, and
   in a case where accumulation and reading out of electric charge when radiation is irradiated is performed once, and accumulation and reading out of electric charge when radiation is not irradiated is repeated k−1 times, with a number of the repetitions in the frame period being a positive integer, the changing unit sets an accumulation period of electric charge not for use in the image generating process so that, $$Tw2 = Tf10 - (k \cdot Tw1 + (k+1) \cdot Tr), \text{ and}$$

$$Tw1 > Tx$$

are satisfied, where Tx is an irradiation period of radiation, Tr is a readout period related to reading out of electric charge, Tf10 is the frame period, Tw1 is the second accumulation period, and Tw2 is the accumulation period of electric charge not for use in the image generating process.

5. The photographing control apparatus according to claim 4, wherein the reference period is, $$Tc = Tx + Tr/k$$

where Tc is the reference period.

6. The photographing control apparatus according to claim 4, wherein the calculating unit calculates the first accumulation period using, $$Tw11 = Tf10/k - Tr$$

where Tw11 is the first accumulation period.

7. The photographing control apparatus according to claim 3, wherein in a case where accumulation and reading out of electric charge when a first radiation is irradiated, accumulation and reading out of electric charge when a second radiation is irradiated, and accumulation and reading out of electric charge when radiation is not irradiated are performed as the repetition in the frame period, the changing unit sets an accumulation period of electric charge not for use in the image generating process so that, $$Tw6 = Tf12 - (2Tw5 + 3Tr), \text{ and}$$

$$Tw5 > Tx$$

are satisfied, where Tx is an irradiation period of the first radiation and the second radiation, Tr is a readout period related to reading out of electric charge, Tf12 is the frame period, Tw5 is the second accumulation period, and Tw6 is the accumulation period of electric charge not for use in the image generating process.

8. The photographing control apparatus according to claim 7, wherein the reference period is, $$Tc=Tx+Tr/3$$

where Tc is the reference period.

9. The photographing control apparatus according to claim 7, wherein the calculating unit calculates the first accumulation period using, $$Tw15=Tf12/3-Tr$$

where Tw15 is the first accumulation period.

10. The photographing control apparatus according to claim 3, wherein in a case where accumulation and reading out of electric charge when a first radiation is irradiated, accumulation and reading out of electric charge when radiation is not irradiated, accumulation and reading out of electric charge when a second radiation is irradiated, and accumulation and reading out of electric charge when radiation is not irradiated are performed as the repetition in the frame period, the changing unit sets an accumulation period of electric charge not for use in the image generating process so that, $$Tw9=Tf13-(2\cdot(Tw7+Tw8)+5Tr), \text{ and}$$

$$Tw7>Txl, Tw8>Txh$$

are satisfied, where Txl is an irradiation period of the first radiation, Txh is an irradiation period of the second radiation, Tr is a readout period related to reading out of electric charge, Tf13 is the frame period, Tw7 is the second accumulation period when the first radiation is irradiated, Tw8 is the second accumulation period when the second radiation is irradiated, and Tw9 is the accumulation period of electric charge not for use in the image generating process.

11. The photographing control apparatus according to claim 10, wherein the reference period is, $$Tc1=Txl+Tr/4, \text{ and}$$

$$Tc2=Txh+Tr/4,$$

where Tc1 is the reference period in a case of the first irradiation, and Tc2 is the reference period in a case of the second irradiation.

12. The photographing control apparatus according to claim 10, wherein the calculating unit calculates the first accumulation period using, $$Tw18=Tf13/4-Tr+(Txl-Txh)/2, \text{ and}$$

$$Tw20=Tf13/4-Tr+(Txh-Txl)/2$$

where Tw18 is the first accumulation period in a case of the first radiation, and Tw20 is the first accumulation period in a case of the second radiation.

13. The photographing control apparatus according to claim 12, the comparing unit compares, $$Tc1>Tw18, \text{ and}$$

$$Tc2>Tw20.$$

14. The photographing control apparatus according to claim 7, wherein the first radiation results from a low voltage and the second radiation results from a high voltage.

15. A control method of a photographing control apparatus that controls a sensor for accumulating and reading out electric charge in order to obtain an image, comprising the steps of:
  deciding a frame period showing an image photographing interval, based on an input of an input unit;
  determining, based on the frame period decided by the deciding step, whether accumulation and reading out of electric charge not for use in an image generating process is set in the frame period; and
  controlling the sensor based on the determination in the determining step.

16. A computer program of instructions stored in a computer-readable medium, the program causing a computer to perform a method comprising the steps of:
  deciding a frame period showing an image photographing interval, based on an input of an input unit;
  determining, based on the frame period decided by the deciding step, whether accumulation and reading out of electric charge not for use in an image generating process is set in the frame period; and
  controlling a sensor based on the determination in the determining step.

* * * * *